United States Patent [19]

Krieg et al.

[11] Patent Number: 4,769,598
[45] Date of Patent: Sep. 6, 1988

[54] APPARATUS FOR ELECTROMAGNETICALLY TESTING THE WALLS OF PIPELINES

[75] Inventors: Gunther Krieg, Karlsruhe; Hartmut Goedecke, Weilburg, both of Fed. Rep. of Germany

[73] Assignee: Kopp AG International Pipeline Services, Lingen, Fed. Rep. of Germany

[21] Appl. No.: 840,126

[22] Filed: Mar. 14, 1986

[30] Foreign Application Priority Data

Mar. 27, 1985 [DE] Fed. Rep. of Germany ....... 3511076

[51] Int. Cl.[4] .................... G01N 27/83; G01N 29/00; G01R 33/12; G01B 17/02
[52] U.S. Cl. ................................ 324/219; 73/601; 73/623; 73/643; 324/226; 324/227; 324/232; 324/242
[58] Field of Search ................ 324/219–221, 324/226, 227, 232, 235, 240–243, 262; 73/601, 623, 643

[56] References Cited

U.S. PATENT DOCUMENTS

| 3,015,063 | 12/1961 | Ownby | 324/221 |
| 3,237,446 | 3/1966 | Wood | 324/226 X |
| 3,593,122 | 7/1971 | Barton et al. | 324/220 |
| 3,850,028 | 11/1974 | Thompson et al. | 324/232 X |
| 4,418,574 | 12/1983 | Flournoy | 324/226 X |
| 4,439,730 | 3/1984 | Kauffman | 324/232 |
| 4,447,777 | 5/1984 | Sharp et al. | 324/220 |
| 4,449,411 | 5/1984 | Suhr et al. | 324/226 X |
| 4,468,619 | 8/1984 | Reeves | 324/235 X |
| 4,477,776 | 10/1984 | Spierer | 324/227 |
| 4,538,108 | 8/1985 | Huschelrath et al. | 324/232 |
| 4,649,343 | 3/1987 | Birchak et al. | 324/220 |
| 4,727,321 | 2/1988 | Huschelrath | 324/226 |

FOREIGN PATENT DOCUMENTS

| 0144456 | 9/1982 | Japan | 324/227 |
| 0208451 | 12/1982 | Japan | 324/226 |

OTHER PUBLICATIONS

The development and application of the intelligent pig; Pipes & Pipelines International, Oct. 1981, pp. 22,23,26,27.

Primary Examiner—Gerard R. Strecker
Attorney, Agent, or Firm—Jordan and Hamburg

[57] ABSTRACT

Apparatus for electromagnetically testing pipeline walls of steel or the like ferromagnetic material which is equipped, for example with a magnetizing coil for leakage-flux measurements, can be extended for ultrasonic measurement which is inductively excited and inductively measured with regard to the travel time as far as a reflecting surface and back, in the disposed in one or more of the pole regions there is a high-frequency current coil for the transmission and/or reception of steep-edged waves which are inductively coupled at the wall of the pipeline. The associated method starts from a stationary magnetic field in which high-frequency current pulses are produced in order to initiate vibrations in the pipe wall through induced currents. The travel time of these vibrations to a reflecting point and back can be measured in order to obtain an indication regarding the intact thickness of the pipe wall.

36 Claims, 6 Drawing Sheets

APPARATUS FOR ELECTROMAGNETICALLY TESTING THE WALLS OF PIPELINES

This invention is concerned with apparatus for and a method of electromagnetically testing the walls of pipelines.

For the non-destructive testing and checking of pipe walls of ferromagnetic material, it is known to induce magnetic fields or eddy-current fields in the pipe wall and to check the fields resulting in the region near the wall for deviations from the norm.

Such a testing system, in connection with apparatus which is driven through a long-distance pipeline, would render possible the detection of faults in the wall of the pipe. Cracks or other defects in the region of the wall interrupt the induction path normally extending in the wall and lead to stray fields through the air which can be reliably recognised.

The examination of the pipeline wall would still be incomplete, however, because weakening of the pipe wall for example, through corrosion for example, could scarcely be detected by this means.

Accordingly, it is the object of the invention to provide apparatus for electromagnetic testing which produces a completed test result with tolerable expenditure on equipment and great reliability, while the apparatus can meet the requirements regarding ease of handling and robustness for rough outdoor operation. It is likewise the object of the invention to provide a corresponding method for the electromagnetic testing of the wall thickness of pipelines.

The present invention is apparatus for electromagnetically testing pipeline walls of steel or the like ferromagnetic material, the apparatus having at least one magnetic system which is equipped with a magnetizing coil and includes the pipeline wall in the magnetic circuit between two poles, and in which disposed in at least one of the pole regions is at least one high-frequency current coil aligned substantially parallel to the pipeline wall to transmit and/or receive steep-edged waves in the ultrasonic range which are coupled inductively at the pipeline wall, at least one of the current coils being equipped with a measuring device to measure delays between transmitted and received pulses.

It has actually been found that it is perfectly possible and practicable to produce deflections and magnetostriction in the pipe wall by means of a magnetic field to such an extent that a vibration travelling predominantly radially through the wall is produced, reflected on the outer wall (or on cracks, projections, and rust cavities situated before it) and passed back to the inner wall of the pipe.

In connection with an applied magnetic field, as a result of the interaction of mechanical material vibrations with an applied magnetic field, here again the result is that a measurable induction occurs, the delay of which in relation to the triggering magnetic pulse is a measure of the travel time of the vibration through the wall and back. This travel time indicates the thickness of the wall, the deviation of which from the specified thickness must be recorded as a fault.

Special dynamic characteristics of a transmission coil are needed for this result, in particular, due to the travel time, which is in the microsecond range, of the transmitted and reflected undulation. Accordingly, a transmission coil with sufficiently short time constants is a prerequisite.

Furthermore, a stationary or quasistationary magnetic field to be superimposed during the transmission and during the reception is a prerequisite, the field being spatially coupled with the transmitted magnetic field in the form of pulses. In order to make available such a stationary magnetic field, recourse may be had, with particular advantage, to an induction system which additionally carries out a measurement of the leakage flux in the region of the inner wall.

In this case, a magnetic system for monitoring the leakage flux is also provided which ensures a field path which is branched in the circumferential direction with two magnetic heads situated diametrically opposite one another. Thus the particularly dangerous longitudinal cracks in the pipes can be located. At the same time, the magnetic heads can easily be developed to form ultrasonic transmitters and to obtain a particularly effective pipe checking—for example in a rotating test system.

Embodiments of the present invention will now be described by way of example, with reference to the accompanying drawings, in which.

Figure 1:
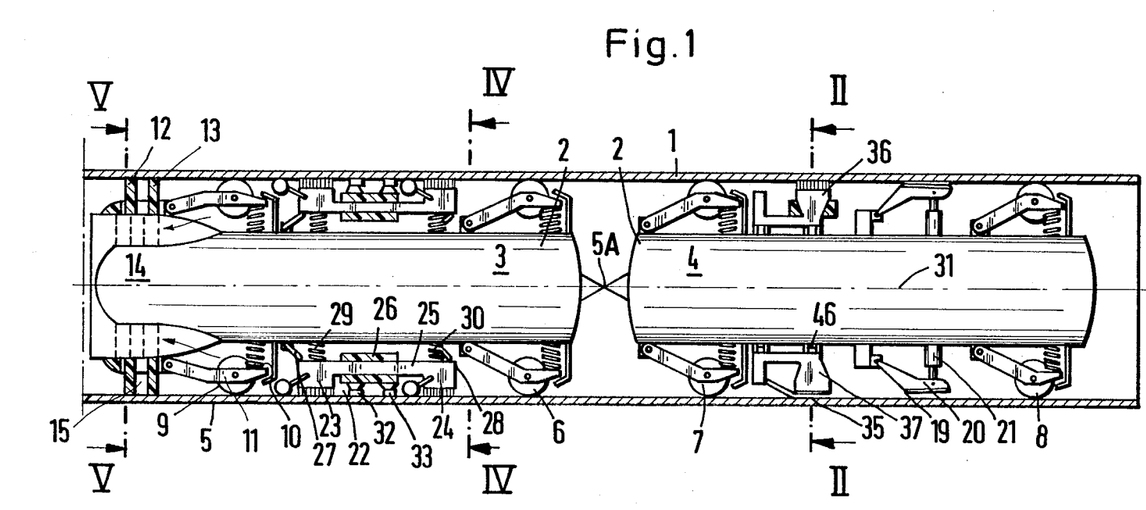
FIG. 1 shows a longitudinal section through a pipe with test apparatus according to the present invention.

In FIG. 1 a portion of a cylindrical steel pipe, designated as a whole by 1, is illustrated in which there is a test apparatus designated as a whole by 2. At the core, the test apparatus consists of two carriages 3 and 4 which are connected to one another by a coupling 5A. The carriages 3 and 4 are substantially cylindrical and have a very much smaller diameter (about half) than the diameter of the pipe 1. They consist of containers of paramagnetic material, such as high-grade steel, brass or plastics material, which containers are rigid in themselves. The hollow interiors are used to accommodate measuring and control equipment.

Various parts, which could come under the heading of "travelling gear" are disposed on the carriages 3 and 4. Thus the carriage 3 has a set of front rollers 9 and a set of rear rollers 6. Similarly, the carriage 4 has a set of front rollers 7 and a set of rear rollers 8. In each of these sets of rollers are at least three, and in this embodiment four, rollers 9 which are distributed uniformly round the circumference and are each carried by a trailing link 11 supported through a spring 10. Thus each of the carriages 3 and 4 is supported on all sides and centred in the middle of the pipe 1.

Figure 5:
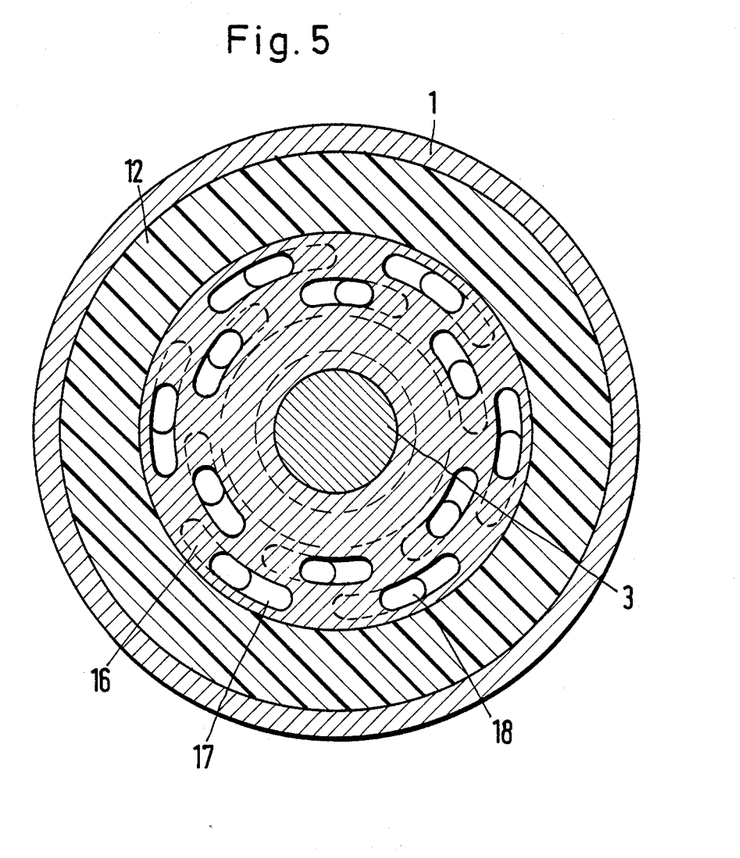
FIG. 5 shows a section on the line V—V of FIG. 1.

Since such apparatus usually operates while fluids are being conveyed through pipelines or are driven forwards by being acted upon by liquid or gas from behind, two sealing discs 12, 13, are provided which bear with their circumference against the inner wall of the pipe 1 and shut off the cross-section in an outer annular region, at the front end of the carriage 3. Formed between these sealing discs 12, 13 and a reduced area nose 14 of the carriage 3 is an annular passage 15 through which liquid or gaseous medium can pass from behind to the front, the flow resistances in the annular passages ensuring an adequate propulsion force. In order to be able to control this propulsion force better, two perforated discs 16 and 17 (situated at the rear in FIG. 5), which are rotatable in relation to one another, are disposed in the annular passage 15 and provide outlet regions 18 which can be widened or constricted. The speed can be monitored by means of a speedometer connected to a roller 9 for example and, depending on this, the apertures 18 can be opened, in the event of too high a speed, or closed, in the event of too low a speed.

The travelling gear also includes a set of brakes 19 which are mounted on the carriage 4 and can be urged outwards against the inner wall of the pipe with pivotable brake runners 20, being actuated through hydraulic operating cylinders 21, if the control capabilities of the annular passage 15 are exceeded or if emergency braking has to be effected.

The power necessary for this control is usually supplied by batteries in the apparatus but may also be picked up continuously as mechanical energy by means of the rollers 9 and be converted into electrical or hydraulic energy by means of dynamos, pumps and the like.

In this manner, the apparatus 2 can be moved through a long-distance pipeline at a controlled speed, over long distances of, for example, 50, 100 or more kilometers in order to check the pipeline with its test equipment as explained below.

For the electromagnetic examination of the inner walls of the pipeline, each of the two carriages 3, 4 has a measuring system for monitoring the stray field and the carriage 3 comprises a measuring system designated as a whole by 22 with eight electromagnets which are distributed uniformly round the circumference, each comprising two measuring heads 23, 24 lying in axial alignment with one another, a yoke 25 connecting the measuring heads and a magnetizing coil 26 for these measuring heads. The electromagnets are each movably suspended on parallelogram links 27, 28 and are pressed outwards against the inner wall of the pipe by springs 29, 30 in order to keep the air-gap leakage losses low.

The field of each electromagnet extends predominantly parallel to a central axis 31 drawn in as an axis of symmetry for the pipe 1 and the apparatus 2.

The field pattern in the pipe would be disturbed if cracks or openings exending transversely or obliquely to the axial direction were to appear at this inner wall of the pipe. The resulting stray field would be picked up by two magnetic sensors 32, 33 which are associated with each electromagnet and are situated between the magnetic heads 23, 24 and which are additionally urged against the inner wall of the pipe by a movable suspension and springs.

Figure 4:
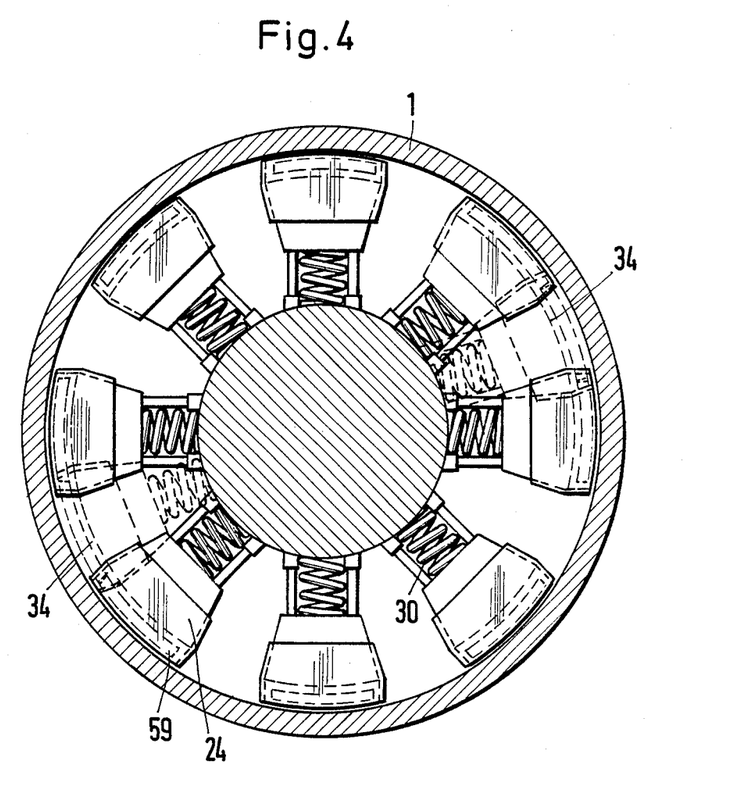
FIG. 4 shows a section on the line IV—IV of FIG. 1.

The spatial distribution of the electromagnets with their magnetic heads 24 at the circumference can be seen in an enlarged illustration in FIG. 4. With eight magnetic heads 24 distributed in the form of a star, narrow monitoring sectors with small gaps result. As indicated by magnetic heads 34 drawn in chain line, the remaining gaps in the sector can be closed by radially staggered magnetic heads, for example in an additional set of axially spaced electromagnets.

Even with these electromagnets distributed without any gaps, however, the particularly dangerous longitudinal cracks in pipelines would scarcely be discovered because they do not hamper the magnetic flux parallel to the axis. In order to detect such longitudinal cracks a novel second measuring system is provided which is disposed on the carriage 4 with spatial and functional separation from the one mentioned above, as a measuring system 35 for longitudinal cracks. This measuring system ensures a magnetic flux extending in the circumferential direction in the pipe 1, for which purpose two magnetic heads 36, 37 situated diametrically opposite one another as north and south poles (see FIG. 2) are directed onto the pipe 1. A branched magnetic field results extending on the one hand over half the circumference towards the right and on the other hand over the half circumference towards the left from north to south. If this is impeded by an open crack at the inner wall as indicated at 38 in FIG. 2, leakage flux 39 emerges in this region and can be measured by available magnetic sensors.

Figure 2:
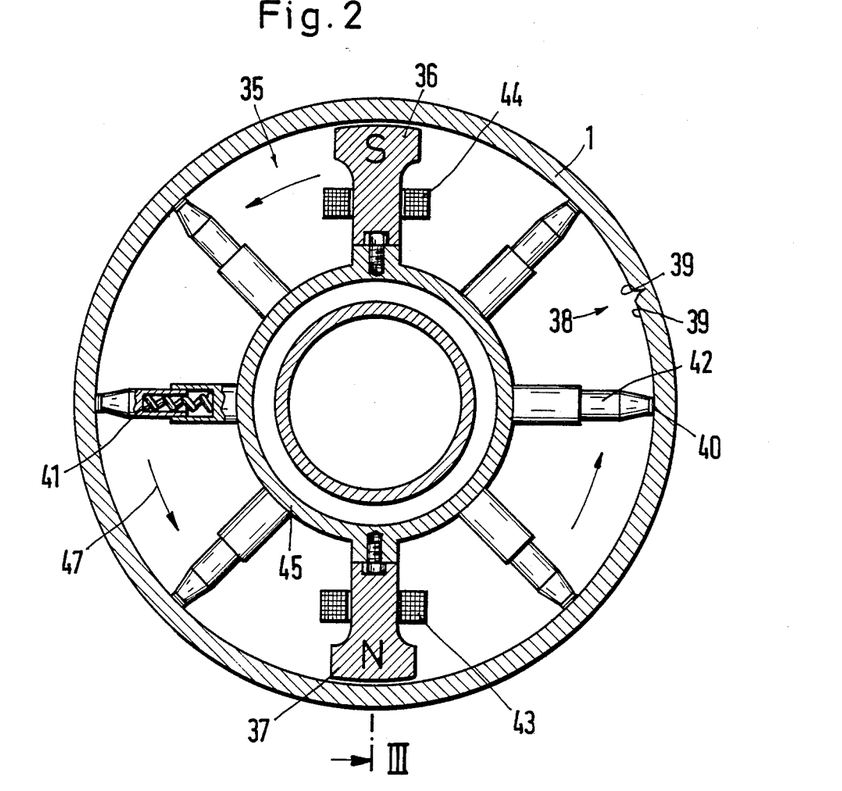
FIG. 2 shows a section on the line II—II of FIG. 1.

For this purpose, six leakage-flux sensors 40 are distributed in the form of a star with angular spacing in relation to one another in the same cross-sectional plane as the poles 36, 37 and are mounted on holding or support means 42 which can be extended telescopically and expanded outwards through an internal spring 41 so that the sensors 40 are in satisfactory contact with the inner wall of the pipe.

Since this arrangement leaves unmonitored sectors between the sensors and since the region of the pipe wall below the pole shoes 36, 37 could not be covered even with sensors set more closely, the system seen in FIG. 2 consisting of two pole shoes (together with magnet coils 43, 44 disposed thereon and the sensors 40 together with their holding means 42) is mounted on an annular support 45 which is rotatable on a rolling-bearing arrangement 46 (see FIG. 1) about the carriage 4 in the direction of the arrows 47 drawn in FIG. 2.

During the advance of the apparatus through a pipe and simultaneous rotation of the magnetic system 35, the sensors 40 move over helical lines which extend the more closely together, the greater the circumferential speed of the support 45 is in relation to the speed of advance of the apparatus 2. With sensor loops exended in area or even groups of such loops connected up parallel to the axis, checks either coinciding in area or overlapping can be made.

Of course only cracks and other surface faults can be detected with the two leakage-flux measuring systems 22 and 35. Weakening of the wall through corrosion from outside or inside and the like cannot be reliably detected thereby.

In view of this, an electrodynamic ultrasonic method has been provided which can be combined with one or both of the stray-field measuring systems present in order to produce vibrations in the pipe wall over the magnetic field and to measure their radial travel time to the outer wall and back as a measure of the wall thickness.

Figure 3:
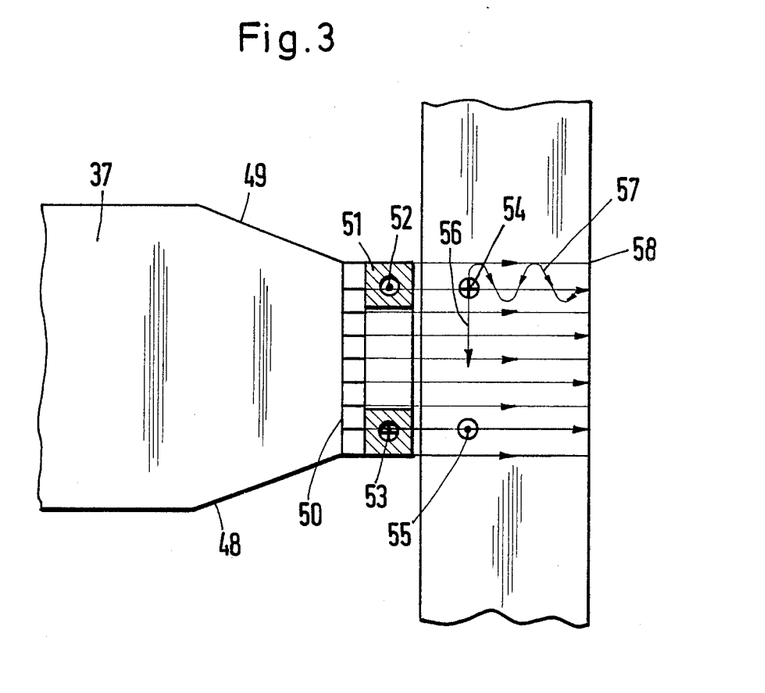
FIG. 3 shows an enlarged section on the line III—III of FIG. 2.

The physical processes are illustrated in FIG. 3 in a detail representation of magnetic head 37 and the adjacent wall of the pipe 1, which is enlarged in comparison with FIG. 2.

The magnetic head 37, which extends with slightly tapered walls 48, 49 towards the pipe 1 in order to achieve a high induction, ends with a plane face 50 with spacing from the pipe 1. An air-cored coil 51 is inserted in the remaining air gap. Whereas the magnetic head 37 furnishes a uniform or at least quasi-stationary induction, the air-cored coil is supplied with powerful and very steep-edged current pulses, the direction of flow of which should be assumed to be in accordance with the direction symbols 52, 53 wherein the numeral 52 represents the head of an arrow to indicate a direction of flow towards the observer and numeral 53 represents the tail of an arrow to indicate a direction of flow away from the observer. Then a mutually induced current loop with the opposite direction of current forms in the adjacent pipe wall in accordance with the direction symbols 54, 55, wherein the numeral 54 represents the tail of an arrow to indicate a direction of flow away from the observer and the numeral 55 represents the head of an arrow to indicate a direction of flow towards the observer. This current flows in the field of the magnetic head 37 and so generates a Lorentz force acting in the pipe, such as that which also causes the propulsion of electric motors with conductors through which a current flows extending transversely to a magnetic field. Such a force is here indicated by an arrow 56.

Under such a force, material vibrations result which are indicated by an undulatory line 57 and are propagated transversely to the pipe, to be reflected on an opposite outer wall 58 of the pipe and to come back into the vicinity of the air-cored coil 51, as a reflected wave after a measurable time of a few microseconds. This coil can now pick up the voltage induction resulting from the material movement in the field of the pole shoe 37 and relay it back to an evaluation circuit. All this presupposes the qualities of a high-frequency current coil for the transmission and the reception. In this case, the amplitude is of less interest than the delay before the appearance of the (first) reflected signal because the local wall thickness is shown from this through the speed of propagation of ultrasonic waves in the material. A typical value for a wall thickness of 10 mm is a delay totalling 3.5 microseconds.

Since the magnetizing head 37 rotates with the support 45, the whole circumference of the pipe is covered in a helical strip. These strips are not covered continuously but, because of the signals transmitted in the form of pulses (with a duration of one microsecond for example) and intervening waiting time for the associated answering pulse, only in a dot pattern which can, however, be regarded as "uninterrupted" with sufficient approximation.

In so far as the helical line omits intermediate regions (extending helically) which are not covered, these can be made smaller by multiple measuring devices. Thus with little additional expense, the magnetic head 36 may additionally be equipped with a pulse generator coil like the air-cored coil 51, the opposite direction of the magnetic flux (from the pipe into the pole shoe) being immaterial.

In so far as this subdivision still appears inadequate, the north or south pole of the measuring system 22 may also be used for a corresponding ultrasonic measurement of wall thickness. In FIG. 4, in the case of the magnetic heads 24, air-cored coils 59 are indicated in chain line, which are likewise in a position to generate steep-edged induction pulses in the microsecond range and, in combination with the DC magnetic field of the pole shoes 24, are able to release ultrasonic waves into the wall, the travel time of which, as far as a reflecting surface and back, can be measured.

The current coils 51 can be provided, at their surfaces directed towards the pipe wall, with a sliding material, that is to say be coated with a suitable polyurethane for example or be cast in this as a whole in order to provide a constant wall clearance by means of spring pressure. Certainly it is one of the particular fundamental advantages of the measuring method that it does not require contact against the pipe wall.

Figure 6:
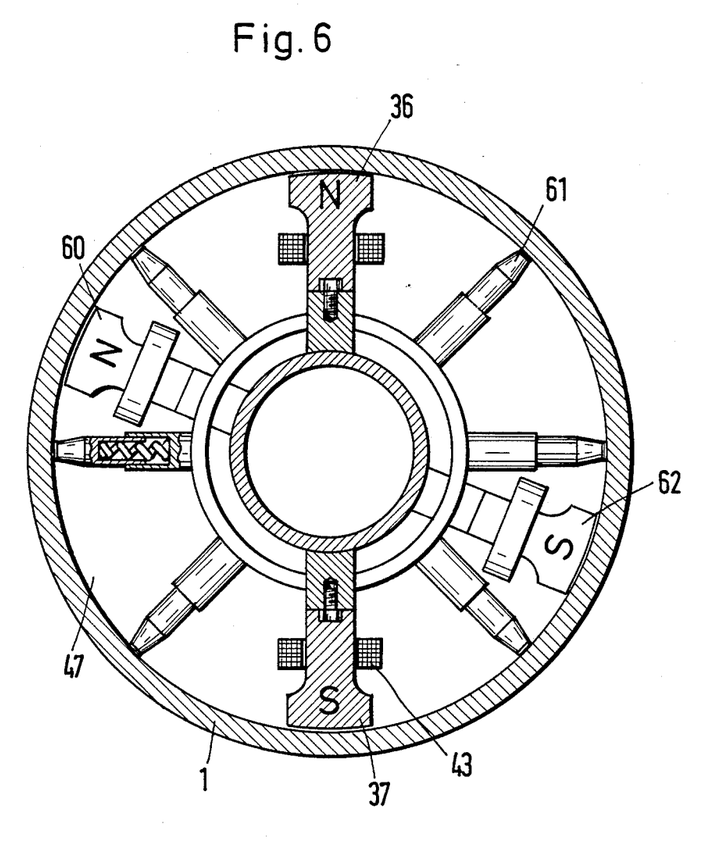
FIG. 6 is a section through a modified embodiment, similar to the section shown in FIG. 2.

In the case of current coils distributed thus closely at the circumference, a current coil in the region of the magnetic heads 36, 37 can also be dispensed with. In a modification, the magnetic heads 36, 37 may also be rigidly connected to the carriage 4 in which case the sensors may still be adapted for rotation or may be set more closely together at the circumference by means of a greater number and density. With magnetic heads 36 and 37 fixed to the apparatus, however, a second angularly offset system 60, 62 of a similar type will generally be necessary, as shown in FIG. 6, because the region swept by the magnetic heads 36, 37 cannot, itself, be monitored for leakage flux by the sensors 61, because there the magnetic field does not extend in the circumferential direction but predominantly radially.

With such a measuring system, a thorough and far-reaching coverage of the pipe wall by magnetic test methods can be effected. The measuring systems can be provided with a robust construction which is necessary for the rough service. From the mechanical point of view, however, the systems can easily be adapted to different pipelines. Thus, because of its movable, spring-supported mounting, the measuring system 22 has a considerable range of use with regard to different pipe diameters. It will be understood, however, that, if necessary, a larger or smaller number of electromagnets should be mounted on another carriage in order to achieve an adaptation to a larger or smaller pipe diameter. The magnetic heads 36, 37 and the sensor holding means 42 are likewise secured to the annular support 45 in such a manner that they can be dismounted so that they can, if necessary, also be transferred to a larger or smaller annular support.

It will be understood that the actuation and interrogation of the magnetic sensors and air-cored coils as well as the supplying of the electromagnets presupposes some expenditure on electrical power and electronic measuring circuits. On the basis of the functions described above, however, these circuits can be realised by circuits which are familiar to the expert. The associated circuitry is accommodated in the carriages 3, 4 in a pressure-tight and hermetically sealed manner and is thus protected.

The current coil 51 and perhaps also the current coil 59 are connected, for the actuation and evaluation, to separate transmitting and receiving devices which prevent disturbances of the receiving circuit by the transmitting circuit by means of suitable blocking devices at the input of the receiving circuit which are effective during the transmitting. It will naturally be understood that transmission and reception coils which are spatially and electrically separated may also be used, for example in a coaxial arrangement in relation to one another. The associated measuring and control circuits in the encapsulated interiors of the articulated apparatus are also adapted to store the measurement results obtained. Furthermore, assuming an adequate possibility for transmission, information for, for example, locating the apparatus or controlling the apparatus, can be exchanged through a telemetry line between the apparatus and one or more outside stations.

Otherwise, however, a storage means should be provided in which case a conversion of the signals into digital values and digital storage should preferably be provided in order to utilize the processing and storage possibilities of the digital technique. This also includes the possibilities of data reduction with selection of the data appearing worth recording.

Together with the particular fault values, information about the position in relation to the length of the pipeline and the point at the circumference should generally also be stored, for which purpose an odometer is usually provided as a mileage indicator which is monitored and reset by means of additional markings (measuring signal from welding seams, radio marking from outside through the pipe).

We claim:

1. Apparatus for electromagnetically testing pipeline walls of ferromagnetic material comprising structure means movably supported on the inside walls of the pipeline such that said structure means is moveable longitudinally along the inside of the pipeline, speed control means on said structure means for controlling the speed of movement of said structural means through said pipeline, first and second magnetic means carried by said structure means for detecting cracks and flaws in said pipeline as said structure means moves longitudinally in said pipeline, said first magnetic means providing one magnetic field operable to detect cracks and flaws extending generally in one direction, said second magnetic means providing a magnetic field operable to detect cracks and flaws extending generally transversely to said one direction, said first and second magnetic means being spaced from one another, and electrodynamic ultrasonic means carried by one of said first and second magnetic means for simulaneously measuring the thickness of the pipeline wall, said electrodynamic ultrasonic means comprising at least one high-frequency current coil substantially aligned with the pipeline wall to transmit and/or receive pulses in the ultrasonic range and which are inductively coupled to the pipeline wall, said at least one current coil having a measuring means for measuring delays between the transmitted and received pulses, whereby the apparatus simultaneously detects cracks and flaws extending both in said one direction and in said other direction and also simultaneously measures the pipeline wall thickness as the structure means continuously moves longitudinally within the pipeline.

2. Apparatus according claim 1 wherein said one magnetic means comprises a magnetizing coil means and at least two pole means such that the pipeline wall is included in a magnetic circuit between said at least two pole means, said at least one high frequency current coil being juxtaposed to at least one of said pole means.

3. Apparatus according to claim 2 wherein said one magnetic means measures the leakage flux, said magnetic means comprising leakage flux sensors juxtaposed to the inner wall of the pipeline and disposed between said at least two pole means.

4. Apparatus according to claim 1 wherein said electrodynamic ultrasonic means further comprises a transmission feeder, said at least one current coil being connected as a transmission coil to said transmission feeder.

5. Apparatus according to claim 1 wherein said at least one current coil produces pulses with a time interval between said pulses, said time interval being greater than the expected maximum delay between said transmitted and received pulses.

6. Apparatus according to claim 2 wherein said pole means are disposed in a substantially common cross-sectional plane, said one magnetic means further comprising leakage-flux sensors to detect cracks and flaws extending in said one direction.

7. Apparatus according to claim 6 wherein said one magnetic means further comprises rotating means for rotating said leakage-flux sensors about an axis coincident with the pipeline axis.

8. Apparatus according to claim 7 wherein said rotating means also rotates said pole means jointly with said leakage-flux sensors.

9. Apparatus according to claim 2 wherein said at least one high frequency current coil is disposed on at least one of said pole means.

10. Apparatus according to claim 2 wherein said at least one high frequency current coil is disposed on the outer radical end portion of at least one of said pole means.

11. Apparatus according to claim 2 wherein said at least one high frequency current coil is spaced from and out of contact with the inside wall of said pipeline.

12. Apparatus according to claim 11 further comprising sliding material means on the outer radical surface of said at least one high frequency current coil.

13. Apparatus according to claim 1 wherein said one magnetic means comprises first and second magnetic heads mounted on said structure means, said first magnetic heads being angularly and longitudinally offset relative to said second magnetic heads.

14. Apparatus according to claim 13 wherein said one magnetic means further comprises rotating leakage-flux sensor means.

15. Apparatus according to claim 13 wherein said first and second magnetic heads extend generally in a generally radial direction, said first and second magnetic heads comprising adjusting means for adjusting the radial length thereof.

16. Apparatus according to claim 14 wherein said leakage-flux sensor means extend in a generally radial direction, said leakage-flux sensor means comprising adjusting means for adjusting the radial length thereof.

17. Apparatus according to claim 13 wherein said structure means comprises interchangeable annular elements, and means detachably securing said magnetic heads to said annular elements.

18. Apparatus according to claim 1 wherein the other of said magnetic means measures leakage-flux, said other magnetic means comprising a plurality of axially aligned pole means.

19. Apparatus according to claim 18 wherein said one magnetic means measures leakage flux, said one magnetic means comprising a plurality of pole means disposed as a ring about the circumference of said structure means.

20. Apparatus according to claim 19 wherein said pole means of said one magnetic means section are disposed in a substantially common cross-sectional plane.

21. Apparatus according to claim 8 wherein said electrodynamic ultrasonic means are circumferentially staggered.

22. Apparatus according to claim 1 wherein said structure means comprises a structure part and detachable means for detachably mounting at least one of said first and second magnetic means to said structure part to provide variation of the annular disposition of said at least one first or second magnetic means.

23. Apparatus according to claim 1 further comprising an electronic data storage system carried by said structure means.

24. Apparatus according to claim 23 further comprising a data processor carried by said structure means and preceding said storage system to sift out needless data.

25. Apparatus according to claim 1 wherein said structure means comprises rollers contacting the inside walls of the structure for rotatably supporting the structure means as the latter moves longitudinally in said pipeline.

26. Apparatus according to claim 25 wherein said speed control means comprises brake means frictionally engageable with the inside wall of the pipeline.

27. Apparatus according to claim 1 wherein said speed control means comprises fluid propelling means utilizing fluid in said pipeline for propelling said structure means along said pipeline.

28. Apparatus according to claim 27 wherein said fluid propelling means comprises sealing means such that the propelling fluid acts against said sealing means to thereby propel the structure means along the longitudinal length of the pipeline, and roller means for movably supporting said structure in said pipeline for longitudinal movement of said structure in said pipeline.

29. Apparatus according to claim 1 wherein a propelling fluid is provided in the pipeline, said speed control means comprising variable-opening means through which said propelling fluid can pass and which is operable to control the speed of movement of the structure through the pipeline by varying the amount of propelling fluid passing through said variable-opening means.

30. Apparatus according to claim 1 wherein said structure means comprises a bearing means having a bearing axis generally coincident with the longitudinal axis of said pipeline, said magnetic means having at least one portion thereof rotatably supported by said bearing means such that said one portion rotates about said bearing axis as said structure means moves in said pipeline.

31. Apparatus according to claim 1 wherein said structure means comprises bearing means for rotatably supporting said one magnetic means, said bearing means having a bearing axis generally coincident with the longitudinal axis of the pipeline such that said one magnetic means rotates about said bearing axis as said structure means moves along said pipeline, said one magnetic means thereby moving along a helical path as said structure means moves along said pipeline.

32. Apparatus according to claim 31 wherein said one magnetic means comprises a plurality of electromagnets circumferentially disposed about a structure means axis which is coincident with the pipeline axis.

33. Apparatus according to claim 32 wherein said other magnetic means comprises parallel links and springs which biasingly urge said electromagnets toward the inner wall of the pipeline.

34. Apparatus according to claim 1 wherein said one magnetic means comprises generally diametrically disposed magnetic heads, said one magnetic means further comprising leakage-flux sensor means provided with a telescopic mounting means and springs for telescopically urging said leakage-flux sensor means radially outwardly toward the inside wall of said pipeline.

35. Apparatus according to claim 1 wherein said structure means comprises two carriages and a coupling coupling said two carriages, said one magnetic means being carried by one carriage, said other magnetic means being carried by the other carriage.

36. Apparatus for electromagnetically testing pipeline walls of ferromagnetic material comprising structure means movably supported on the inside walls of the pipeline such that said structure means is moveable longitudinally along the inside of the pipeline, speed control means on said structure means for controlling the speed of movement of said structural means through said pipeline, first and second magnetic means carried by said structure means for detecting cracks and flaws in said pipeline as said structure means moves longitudinal in said pipeline, said first magnetic means providing one magnetic field operable to detect cracks and flaws extending generally in one direction, said second magnetic means providing another magnetic field operable to detect cracks and flaws extending generally transversely to said one direction, said first and second magnetic means being spaced from one another, and electrodynamic ultrasonic means carried by one of said first and second magnetic means for simultaneously measuring the thickness of the pipeline wall, said structure means comprises bearing means for rotatably supporting said one magnetic means, said bearing means having a bearing axis generally coincident with the longitudinal axis of the pipeline such that said one magnetic means rotates about said bearing axis as said structure means moves along said pipeline, said one magnetic means thereby moving along a helical path as said structure means moves along said pipeline, said one magnetic means comprises a magnetizing coil means and at least two pole means such that the pipeline wall is included in a magnetic circuit between said at least two pole means, said electrodynamic ultrasonic means further comprising at least one high-frequency current coil juxtaposed to at least one of said pole means and substantially aligned with the pipeline wall to transmit and/or receive pulses in the ultrasonic range and which are inductively coupled to the pipeline wall, said at least one current coil having a measuring means for measuring delays between the transmitted and received pulses, whereby the apparatus simultaneously detects cracks and flaws extending both in said one direction and in said other direction and also simultaneously measures the pipeline wall thickness as the structure means continuously moves longitudinally within the pipeline.

* * * * *